(12) United States Patent
Redl et al.

(10) Patent No.: US 7,091,325 B2
(45) Date of Patent: *Aug. 15, 2006

(54) FIBRIN/FIBRINOGEN-BINDING CONJUGATE

(75) Inventors: Heinz Redl, Vienna (AT); Walter Fuerst, Vienna (AT); Rudolf Kneidinger, Vienna (AT); Sam L. Helgerson, Altadena, CA (US); Douglas Looker, Ft. Lupton, CO (US); Elisabeth M. Inman, Pasadena, CA (US); Jane P. Richards, Longmont, CO (US); Catalina Wong, Los Angeles, CA (US)

(73) Assignees: Baxter Aktiengesellschaft, Vienna (AU); Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/749,832

(22) Filed: Dec. 30, 2003

(65) Prior Publication Data
US 2004/0191261 A1    Sep. 30, 2004

Related U.S. Application Data

(63) Continuation of application No. 09/963,156, filed on Sep. 25, 2001, now Pat. No. 6,713,453, which is a continuation-in-part of application No. 09/669,240, filed on Sep. 25, 2000, now Pat. No. 6,506,365.

(51) Int. Cl.
| | |
|---|---|
| A61K 31/7088 | (2006.01) |
| A61K 38/17 | (2006.01) |
| A61K 39/395 | (2006.01) |
| C07H 21/00 | (2006.01) |
| C07K 14/435 | (2006.01) |

(52) U.S. Cl. .............. 530/391.1; 424/9.34; 424/9.4; 424/178.1; 514/2; 514/12; 514/44; 530/391.3; 530/391.7; 530/402; 530/408; 530/409; 530/410; 536/23.1

(58) Field of Classification Search ............ 514/2, 514/8, 12, 21, 43, 44; 536/23.1; 424/1.49, 424/1.53, 1.69, 9.34, 9.341, 9.4, 9.411, 178.1, 424/179.1, 180.1, 181.1, 182.1, 425, 426, 424/484, 486; 530/382, 391.1, 391.3, 391.5, 530/391.7, 391.9, 402, 408, 409, 410
See application file for complete search history.

(56) References Cited

U.S. PATENT DOCUMENTS 4,359,049 A    11/1982   Redl et al. ............... 604/82

(Continued)

FOREIGN PATENT DOCUMENTS

CA    1 168 982    6/1984

(Continued)

OTHER PUBLICATIONS

Greenberg et al. Covalent Immobilization of Recombinant Human alpha-a-beta-3 Integrin on a Solid Support with Retention of Functionality. Analytical Biochemistry. 1999, vol. 266, pp. 153-164.*

(Continued)

*Primary Examiner*—Jeffrey Edwin Russel
(74) *Attorney, Agent, or Firm*—Townsend and Townsend and Crew; Janice Guthrie

(57) ABSTRACT

A fibrin/fibrinogen binding conjugate for forming a depot for the sustained release of a pharmaceutically active substance from a fibrin clot. The conjugate comprises a fibrin/fibrinogen binding moiety bound to a pharmaceutically active substance either directly or via an intervening substance capturing moiety such as an antibody. The conjugate can also be a recombinant fusion protein comprising a fibrin/fibrinogen binding moiety such as $VEGF_{165}$ C-terminal domain fused to a wound-healing substance such as leptin.

13 Claims, 13 Drawing Sheets

U.S. PATENT DOCUMENTS

| | | | |
|---|---|---|---|
| 4,393,041 A | 7/1983 | Brown et al. | 424/426 |
| 4,631,055 A | 12/1986 | Redl et al. | 604/82 |
| 4,735,616 A | 4/1988 | Eibl et al. | 604/191 |
| 5,019,572 A * | 5/1991 | Claremon et al. | 514/12.07 |
| 5,217,705 A | 6/1993 | Reno et al. | 424/1.1 |
| 5,328,996 A | 7/1994 | Boyle et al. | 536/23.1 |
| 5,332,671 A | 7/1994 | Ferrara et al. | 435/240.1 |
| 5,364,612 A | 11/1994 | Goldenberg | 424/1.53 |
| 5,629,287 A * | 5/1997 | Brown et al. | 514/8 |
| 5,688,935 A | 11/1997 | Stephens et al. | 536/23.1 |
| 5,792,742 A | 8/1998 | Gold et al. | 514/2 |
| 5,869,616 A * | 2/1999 | Vogel et al. | 530/380 |
| 6,110,721 A * | 8/2000 | Gibbs et al. | 435/214 |
| 6,506,365 B1 | 1/2003 | Redl et al. | 424/9.4 |
| 6,613,563 B1 * | 9/2003 | Sosnowski et al. | 435/320.1 |
| 6,713,453 B1 * | 3/2004 | Redl et al. | 514/21 |

FOREIGN PATENT DOCUMENTS

| | | |
|---|---|---|
| EP | 0 292 472 B1 | 5/1988 |
| WO | WO 96/06641 A1 | 3/1996 |
| WO | WO 98/43686 | 10/1998 |
| WO | WO 99/40947 A2 | 8/1999 |
| WO | WO 01/10479 A1 | 2/2001 |

OTHER PUBLICATIONS

Frank et al., "Leptin enhances wound re-epithelialization and constitutes a direct function of leptin in skin repair," *The Journal of Clinical Investigation*, 106(4):501-509 (2000).

Houck et al., "Dual Regulation of Vascular Endothelial Growth Factor Bioavailability by Genetic and Mechanisms," *The Journal of Biological Chemistry*, 267(36):26031-26037 (1992).

Kurokawa, et al. "Enhanced Fibrinolysis by a Bispecific Monoclonal Antibody Reactive to Fibrin and Tissue Plasminogen Activator" *Biotechnology*, 7:1163-1167 (Nov. 1989).

Markland et al., "Iterative Optimization of High-Affinity Protease Inhibitors Using Phase Display, 1. Plasmin," *Biochemistry*, 35:8045-8057 (1996).

Sahni et al., "Vascular Endothelial Growth Factor Blinds to Fibrinogen and Fibrin and Stimulates Endothelial Cell Proliferation" *Blood*, 96:3772-3778 (2000).

Sierra-Honigmann et al., "Biological Action of Leptin as an Angiogenic Factor," *Science*, 281:1683-1686 (1998).

Tischer et al., "The Human Gene Vascular Endothelial Growth Factor," *Journal of Biological Chemistry*, 266(18):11947-11954 (1991).

* cited by examiner

Leptin-VEGF-HisTag Fusion Protein (M)$^{+1}$VPIQKVQDDTKTLIKTIVTRINDISHTQSVSSKQKVT
GLDFIPGLHPILTLSKMDQTLAVYQQILTSMPSRNVIQIS
NDLENLRDLLHVLAFSKSCHLP[E]ASGLETLDSLGGVLEAS
GYSTEVVALSRLQGSLQDMLWQLDLSPG(C)RPKKDRARQEN
PCGPCSERRKHLFVQDPQTCKCSCKNTDSRCKARQLELNE
RTCRCDKPRRHHHHHH$^{+214}$ Key:
( ) initiator methionine position -1
☐ W100E mutation
○ overlapping cysteine residue - junction between leptin and VEGF
| plasmin cleavage site
— His Tag

Figure 11

SEQUENCE LISTING

<160> NUMBER OF SEQ ID NOS: 1

<210> SEQ ID NO 1
<211> LENGTH: 214
<212> TYPE: PRT

```
<213> ORGANISM: Artificial Sequence
<220> FEATURE:
<223> OTHER INFORMATION: Description of Artificial Sequence:
      leptin-VEGF-165 C-terminal-His tag fusion protein
<220> FEATURE:
<221> NAME/KEY: INIT_MET
<222> LOCATION: (1)
<223> OTHER INFORMATION: initiator Met (position -1)
<220> FEATURE:
<221> NAME/KEY: PEPTIDE
<222> LOCATION: (2)..(147)
<223> OTHER INFORMATION: leptin sequence
<220> FEATURE:
<221> NAME/KEY: MUTAGEN
<222> LOCATION: (101)
<223> OTHER INFORMATION: W100E mutation
<220> FEATURE:
<221> NAME/KEY: SITE
<222> LOCATION: (147)
<223> OTHER INFORMATION: final residue in full-length leptin overlaps
      with first Cys in VEGF-165 C-terminal domain
<220> FEATURE:
<221> NAME/KEY: SITE
<222> LOCATION: (153)..(154)
<223> OTHER INFORMATION: plasmin cleavage site
<220> FEATURE:
<221> NAME/KEY: PEPTIDE
<222> LOCATION: (147)..(165)
<223> OTHER INFORMATION: VEGF-165 C-terminal domain (C104-R165)
<220> FEATURE:
<221> NAME/KEY: SITE
<222> LOCATION: (209)..(214)
<223> OTHER INFORMATION: His tag

<400> SEQUENCE: 1

Met Val Pro Ile Gln Lys Val Gln Asp Asp Thr Lys Thr Leu Ile Lys
  1               5                  10                  15

Thr Ile Val Thr Arg Ile Asn Asp Ile Ser His Thr Gln Ser Val Ser
                 20                  25                  30

Ser Lys Gln Lys Val Thr Gly Leu Asp Phe Ile Pro Gly Leu His Pro
             35                  40                  45

Ile Leu Thr Leu Ser Lys Met Asp Gln Thr Leu Ala Val Tyr Gln Gln
 50                  55                  60

Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys His Leu Pro Glu Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
            115                 120                 125

Arg Leu Gln Gly Ser Leu Gln Asp Met Leu Trp Gln Leu Asp Leu Ser
130                 135                 140

Pro Gly Cys Arg Pro Lys Lys Asp Arg Ala Arg Gln Glu Asn Pro Cys
145                 150                 155                 160

Gly Pro Cys Ser Glu Arg Arg Lys His Leu Phe Val Gln Asp Pro Gln
                165                 170                 175

Thr Cys Lys Cys Ser Cys Lys Asn Thr Asp Ser Arg Cys Lys Ala Arg
            180                 185                 190

Gln Leu Glu Leu Asn Glu Arg Thr Cys Arg Cys Asp Lys Pro Arg Arg
            195                 200                 205

His His His His His His
    210
```

FIBRIN/FIBRINOGEN-BINDING CONJUGATE

CROSS REFERENCE TO RELATED APPLICATIONS

This is a CON of Ser. No. 09/963,156 filed Sep. 25, 2002, now U.S. Pat. No. 6,713,453, which is a continuation-in-part of application Ser. No. 09/669,240, filed Sep. 25, 2000 now U.S. Pat. No. 6,506,365.

FIELD OF THE INVENTION

The present invention relates to conjugates having specific utility as depots for pharmaceutically active substances.

BACKGROUND OF THE INVENTION

Providing drug depots for sustained-release action is essential for efficient treatment of patients which require a steady administration of specific pharmaceutically active substances, especially if the drug is desired to be applied inside the body. A prerequisite for an adequate drug depot is that the release of the pharmaceutically active substance from such a depot is controllable by specific retardation processes. This implies that the pharmaceutically active substance has to be connected to the depot matrix either in a reversible or an irreversible way.

The matrix to which the pharmaceutically active substance is bound should not only have an affinity to the active substance but also have biocompatible properties. Preferably, such depot matrices are biodegradable within the body of the patient so that no further treatment of the patient for removing the emptied depot is necessary.

Because of their advantageous biological properties especially fibrin gels have been proposed as preferred drug depot matrices (see e.g. AT 369 990). Fibrin gels are easy to prepare, have good biocompatibility and their biological degradation inside the body can be regulated. However, due to the hydrated and wide porous structure of fibrin, diffusion of pharmaceutically active substances occurs with a rate much too fast for most purposes even if the fibrin gel is highly cross-linked by excess addition of its natural cross-linking effector, factor XIII.

In preliminary experiments carried out for the present invention it could be shown that different proteins, such as β-galactosidase are completely released from a fibrin gel within three days or less.

It has therefore been proposed to covalently link bioactive factors to a fibrin network by linking a transglutaminase substrate domain to a bioactive factor using factor XIIIa activity (WO98/43686). However, covalent binding of the drug of interest to the fibrin network may result in a binding too strong to allow a sufficient release of the drug to the patient. Not all drugs are compatible with covalent binding. Moreover, the fibrin clot might become unstable because cross-linking sites are used by the transglutaminase substrates, which are essential for this reaction.

It is therefore an object to provide a drug depot having satisfactory biocompatibility and a regulatable half-life in the patient's body.

It is a further object of the present invention to provide for an alternative drug depot based on fibrin, especially without altering the active substance or using enzymatic activity for its linkage.

Another object of the present invention is to provide a drug depot with capacity for efficient retardation of diffusion of the biologically active substance compared to the release time of this drug by diffusion from a standard fibrin gel.

SUMMARY OF THE INVENTION

These objects are solved by a fibrin/fibrinogen-binding conjugate comprising a fibrin/fibrinogen-binding moiety, a substance capturing moiety capable of reversibly binding to a pharmaceutically active substance, and a pharmaceutically active substance, wherein said fibrin/fibrinogen-binding moiety is bound to said substance capturing moiety.

With the conjugate according to the present invention, binding partners with affinity to fibrin or fibrinogen are used to link binding partners of pharmaceutically active substances to a fibrin gel. Due to these fibrin or fibrinogen binding moieties, the conjugates are bound sufficiently to the fibrin matrix so that elution of the pharmaceutically active substance is not possible by simple diffusion, but mainly dependent on the affinity of the fibrin/fibrinogen-binding moiety to fibrin and on the binding affinity of the substance capturing moiety to the pharmaceutically active substance.

The binding of the fibrin/fibrinogen-binding moiety to the substance capturing moiety can be covalently, e.g. using chemical linkers such as 1-ethyl-3-(3-dimethylaminopropyl) carbodiimide (EDC) known in the art, or by electrostatic forces.

In another embodiment of the invention, the conjugate is a fusion protein comprising a fibrin/fibrinogen binding moiety covalently linked to a pharmaceutically active, substance, without an intervening substance capturing moiety.

The term "fibrin/fibrinogen-binding moiety" relates to a binding moiety which is capable of binding either to (1) fibrin or to (2) both fibrinogen and fibrin. If the binding capacity is for both fibrin and fibrinogen, it is possible to form the fibrin gel with fibrinogen molecules which are already "loaded" with the present conjugates to allow a homogeneous formation of the drug depot and a homogeneous distribution of the conjugate, and therefore the pharmaceutical throughout the fibrin drug depot.

BRIEF DESCRIPTION OF THE DRAWINGS

FIG. 11 shows the amino acid sequence of the leptin-VEGF$_{165}$ C-terminal-His tag fusion protein [SEQ ID NO:1].

DETAILED DESCRIPTION OF THE INVENTION

Figure 1:
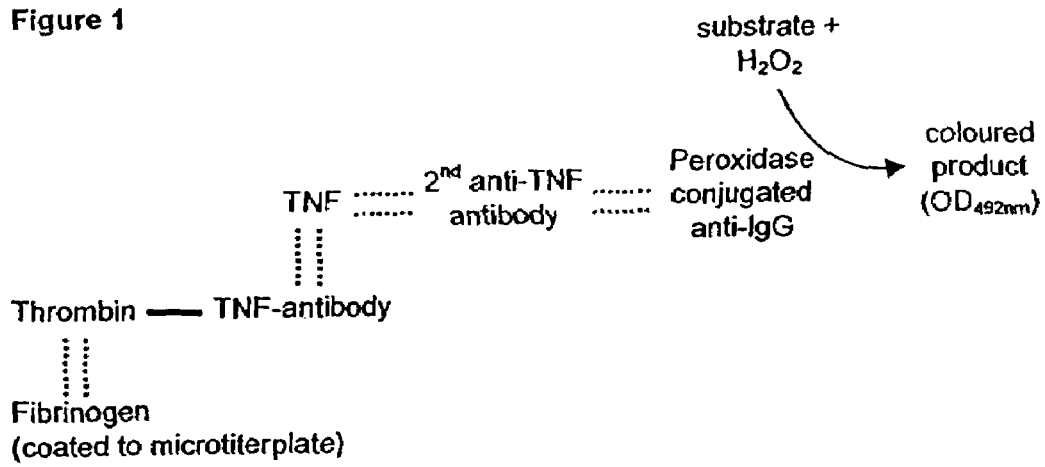
FIG. 1 shows the ELISA-sandwich system for the detection of the covalent binding (–) of TNF antibody and thrombin as well as the binding affinities (:::) to fibrin/fibrinogen and TNF, respectively.

The present invention provides a biomatrix containing a conjugate which is able to bind to a fibrin gel and preferably to fibrinogen as well. The conjugate's binding affinity to fibrinogen is transferred to the binding of fibrin after cleavage of the fibrinogen to fibrin.

One conjugate according to the present invention comprises: a binding moiety which binds to fibrin/fibrinogen, a substance capturing moiety capable of reversibly binding to a pharmaceutically active substance, and the pharmaceutically active substance. According to the present invention the fibrin/fibrinogen-binding moiety is bound to the substance capturing moiety, preferably covalently. For example a fibrin/fibrinogen-binding protein or a part thereof which binds to fibrin/fibrinogen may be bound or coupled to a substance capturing moiety. This coupling may be accomplished by chemical linkers, by recombinant DNA technology, by peptide synthesis or combinations of these techniques.

Another conjugate of the invention comprises a fibrin/fibrinogen binding moiety covalently linked directly to a pharmaceutically active substance, without an intervening substance capturing moiety. A depot formed with this conjugate provides sustained release of the pharmaceutically active substance based on the release kinetics of the fibrin/fibrinogen binding moiety from fibrin, as well as the natural dissolution of the fibrin clot over time. In this instance, the pharmaceutically active substance retains its activity even when it remains covalently linked to the fibrin/fibrinogen binding moiety.

The fibrin/fibrinogen-binding moiety may be derived from naturally occurring (e.g. physiological) binding proteins, such as thrombin, fibronectin, bacterial fibrinogen binding proteins, basic fibroblast growth factor, integrins, tissue-type plasminogen activator, VEGF$_{165}$, and similar proteins exhibiting at least one fibrin/fibrinogen-binding moiety.

In a further embodiment a nucleic acid, particularly DNA may be used as a fibrin/fibrinogen-binding moiety. This DNA need not have a coding function and therefore can even be of random sequence although care has to be taken to avoid a possibly inflammatory motif, especially a CpG-motif, within the sequence. For the purposes of the present invention DNA is used in any form, which means single- or double stranded DNA, linear or circular DNA, as a fibrin/fibrinogen-binding moiety.

For the present conjugate, proteins may either be used in their physiological form or in a processed form. For example, such physiological binding partners may be processed by known biochemical techniques, in order to provide at least the fibrin/fibrinogen-binding parts of these proteins. Alternatively, the parts known to bind to fibrin/fibrinogen can also be provided by recombinant DNA technology. For many fibrin/fibrinogen-binding proteins a three-dimensional structure has been described or proposed, enabling one of skill in the art to select those parts of these proteins which are relevant for fibrin/fibrinogen-binding for use in the present invention. Other substances with binding affinity for fibrin/fibrinogen may be analyzed for their putative fibrin/fibrinogen-binding sites based on known three-dimensional models of the above mentioned proteins, e.g. by sequence analysis, if such substances are proteins or protein derivatives or selection by phage display.

The choice of the substance capturing moiety or the directly bound pharmaceutically active substance is essentially dependent on the pharmaceutically active substance to be administered by the fibrin depot. Suitable pairs of substance capturing moieties and pharmaceutically active substances are known in the art.

For example a substance-capturing moiety may be an antibody, a receptor or a part thereof, which specifically recognizes and reversibly binds the pharmaceutically active substance of interest (e.g. as an antigen or ligand). Herein, the term "antibody" includes a complete antibody of any class, comprising the constant domain as well as the variable antigen binding domain, as well as parts of antibodies or antibody derived molecules, e.g. fragments or recombinant constructs. Indeed, most of the parts of such "classical" antibodies may be omitted as long as the essential moiety, namely the variable binding region, which allows the binding of the pharmaceutically active substance, is present.

A further example of a substance capturing moiety may be the group of antibody binding molecules, e.g. bacterial proteins like protein A or protein G or Fc-receptor of macrophages, as well as fragments or recombinant constructs thereof.

According to a preferred-embodiment of the present invention monoclonal antibodies or the antigen binding regions of monoclonal antibodies are used as substance capturing moieties. Further, coupling of such a monoclonal antibody or parts thereof to a fibrin/fibrinogen-binding moiety, especially a fibrin binding protein, may be established by classical protein chemistry.

The present invention may be adapted for all pharmaceutically active substances possible, especially for those for which a suitable binding partner is already known (e.g. antigen/antibody, receptor/ligand, complex partners). The binding partner to be applied as a drug is bound to the conjugate only via its individual corresponding binding partner, the latter being covalently coupled to the fibrin/fibrinogen-binding moiety.

Herein the term "reversible binding" refers to non-covalent binding based on electrostatic forces which confer an affinity between the substance capturing moiety and the pharmaceutically active substance, whereby the pharmaceutically active substance is released over time to diffuse from the fibrin clot.

Preferred pharmaceutically active substances to be used in the present conjugate are antibiotics, growth factors, receptors for tissue components, tissue adhesive substances, anti-tumor agents, cell adhesive substances, nucleic acids, plasma proteins, anti-proteases, fibrinolysis-inhibitors, hormones, heparinoids, wound-healing substances and mixtures thereof. When the pharmaceutically active substance is a fibrinolysis inhibitor such as aprotinin, as part of the inventive conjugate, the clot to which the conjugate is bound will last longer than a clot which merely contains free aprotinin, which would readily diffuse out of the clot.

These substances may either be directly pharmaceutically active or allow an improved action of another pharmaceutically active substance, which may be applied simultaneously or separately with the present drug depot. For example, receptors for tissue components or tissue adhesive substances may be applied which allow an improved performance of a tissue adhesive based on fibrinogen. Other examples which change the adhesive properties of a tissue adhesive are substances which may be provided with the present conjugate. If applied together with a "classical" tissue adhesive, the presence of such pharmaceutically active substances which have an influence on the adhesion properties may influence the adhesive or non-adhesive capacity of the fibrinogen tissue adhesive to specific tissues or cells. Other substances, such as nucleic acids or anti-tumor agents may also be applied together with a specific fibrin/fibrinogen basis to form a depot for these substances at the site necessary for a desired effect. Also substances useful for image based diagnostic methods e.g. for X-rays or magnetic resonance induction (MRI) or colors may be used according to the present invention.

According to a preferred embodiment of the present invention the conjugate or the bifunctional molecule is designed for the incorporation in a "classical" tissue adhesive system. Such a system usually comprises a fibrinogen and a thrombin containing preparation similar to a "one-" or "two component" glue resulting in fibrin formation at the site of application or a preformed fibrin preparation, e.g. a fibrin fleece. The formed fibrin clot or the fibrin fleece allows e.g. wound closure or tissue adhesion. Further ingredients in this system are e.g. Factor XIII (as a cross-linker), fibrinolysis-inhibitors, etc (see e.g. Fibrin Sealing in Surgical and Non-Surgical Fields, Schlag G., Redl H. editors, Vols. 1–9).

The fibrin/fibrinogen-binding moiety and the substance-capturing moiety are preferably covalently bound by a linker substance, especially linker substances which are used and have proven to be successfully applied in protein chemistry. This preferred embodiment is especially suited if enhanced flexibility of the moieties is desired.

Although the pharmaceutically active form of the conjugate according to the present invention comprises the pharmaceutically active substance, the present invention also relates to the conjugate without the drug. Such a "naked" conjugate may be easily transformed into a pharmaceutically active form by "loading" the conjugate comprising the fibrin/fibrinogen-binding moiety and the substance-capturing moiety with the individual drug wherefore the substance-capturing moiety has been designed.

A specific embodiment of the present invention relates to a conjugate wherein the drug to be applied has been designed to carry a fibrin/fibrinogen containing moiety. According to this aspect of the present invention, the substance-capturing moiety may be omitted. Also this conjugate may be designed by protein chemistry, peptide synthesis and/or recombinant technology by combining a fibrin/fibrinogen-binding moiety with the pharmaceutically active substance, e.g. by direct covalent binding or by binding with suitable linker substances. Also these conjugates, which do not need a separate "loading" with the pharmaceutically active substance, may be used in a common tissue adhesive system as described above.

Figure 10:
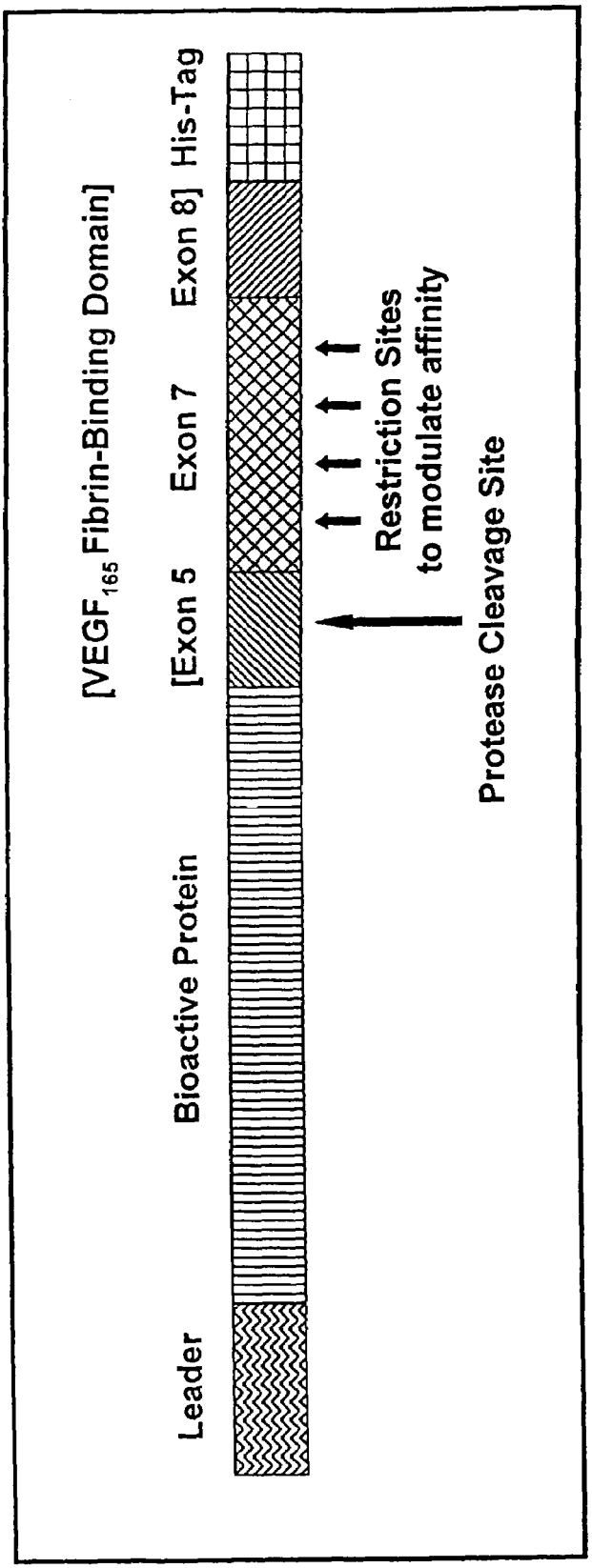
FIG. 10 depicts the general scheme of a fibrin-binding recombinant fusion protein comprising the VEGF$_{165}$ C-terminal fibrin-binding domain linked to a pharmaceutically active protein.

A preferred fibrin/fibrinogen binding conjugate is based on the present inventors' discovery that the C-terminal domain of $VEGF_{165}$ is responsible for the fibrin-binding capacity of that molecule. Herein, the term "C-terminal domain of $VEGF_{165}$" refers to amino acid residues C104-R165 as depicted in U.S. Pat. No. 5,332,671, FIGS. 10a and 10b (Ferrara and Leung). $VEGF_{165}$ is further described in Tischer et al, J. Biol. Chem. (1991) 266:11947–11954; Sahni et al, Blood (2000) 96:3772–3778; and Houck et al, J. Biol.Chem. (1992) 267:26031 –26037). The fibrin-binding domain of this conjugate is not limited to the natural amino acid sequence coded for by exons 5, 7, and 8, as depicted in FIG. 10 of the present document. The fibrin-binding properties of the resulting fusion protein can be altered in order to increase or decrease the release kinetics from the fibrin depot by adding, deleting, or mutating specific amino acid residues in the $VEGF_{165}$ C-terminal domain. $VEGF_{165}$ also contains a natural plasmin cleavage site at the beginning of its C-terminal domain. Thus the C-terminal domain of $VEGF_{165}$ can be used to form a fusion protein with a pharmaceutically active substance, without the need for a "substance-binding moiety" between the fibrin binding moiety and the pharmaceutically active substance. When the conjugate is incorporated into a fibrin clot at a wound site, the natural plasminogen in the patient's plasma entering the wound is converted to plasmin, which in turn cleaves the fusion protein to release the pharmaceutically active substance, allowing its diffusion from the clot. Another mechanism for release is based on the dissociation rate of the $VEGF_{165}$ C-terminal domain from fibrin; according to this mechanism, the entire conjugate is released and diffuses from the clot, allowing the pharmaceutical substance to act at the wound site, outside the clot. The following are examples of pharmaceutically active substances which can be fused to the C-terminal moiety of $VEGF_{165}$:

cytokines, growth factors, and wound-healing substances such as leptin (Frank et al, J. Clin. Invest. (2000) 106:501–509; Sierra-Honigmann et al., Science (1998) 281:1683–1686), IL-8, MCP-1, and PF-4.

antibiotic peptides such as magainins, defensins, and granulysin.

fibrinolysis inhibitors such as aprotinin and Kunitz domains of human lipoprotein-associated coagulation inhibitor (LACI-D1; Markland et al., Biochemistry (1996) 35:8045–8057).

The pharmaceutically active substance thus released can serve to direct the growth, migration, and differentiation of specific cell types, thus enhancing wound healing and neovascularization during tissue repair.

According. to another aspect the present invention relates to a kit for forming a depot for a pharmaceutically active substance comprising a tissue adhesive based on fibrinogen and a conjugate according to the present invention. The conjugate may be provided in a separate form ready to be mixed before medical use. The "ready to use" mixture of the tissue adhesive based on fibrinogen and the conjugate according to the present invention may be applied with means and methods as already. known in the art for "classical" tissue adhesives, especially with the fibrinogen component of such adhesives. This fibrinogen component may be mixed in a known way with a component containing an activity for processing fibrinogen to fibrin, preferably a thrombin preparation.

A kit according to the present invention may therefore also contain suitable devices for administering the tissue adhesive and the conjugate and optionally the fibrinogen to fibrin processing activity. Examples for such devices are described in EP 0 037 393 A, EP 0 315 222 A, EP 0 156 098 A, EP 0 210 160 A and EP 0 292 472 A, which are incorporated herein by reference.

According to another aspect the present invention relates to a method for producing a depot of a pharmaceutically active substance comprising providing a conjugate according to the present invention, administering this conjugate at a depot site together with a fibrinogen preparation, allowing processing of said fibrinogen to fibrin whereby a fibrin clot is formed, and allowing binding of the conjugate to said fibrinogen or the fibrin clot formed.

Processing of the fibrinogen to fibrin may either be performed by thrombin already being present at the site of administration or by an exogenously added fibrinogen processing activity. Apart from thrombin or thrombin derived proteases, other proteases such as streptylase, protease III and venom proteases like e.g. baxotropin, may be used for cleaving the fibrinogen molecule. The binding of the conjugate to fibrin/fibrinogen may take place after forming of the fibrin clot. However, it is preferred to allow this binding process at an earlier stage, e.g. during the fibrinogen processing step or (most preferred) even before, so that binding of the conjugate according to the present invention takes place at the fibrinogen level. This results in a fibrin depot which has a homogeneous distribution of conjugate throughout the whole depot. On the other hand, if the conjugate is intended to be located mainly on the surface of the fibrin depot, binding of the conjugate should be allowed after forming of the fibrin clot.

Another aspect of the present invention relates to a depot for a pharmaceutically active substance, comprising a conjugate according to the present invention and fibrin (e.g. a suitable fibrin matrix). Such a depot is e.g. obtainable by administration of a conjugate according to the present invention to a fibrin network base.

Yet still another object of the present invention is drawn to a method for treating a patient suffering from a pathological state, said pathological state being treatable with a pharmaceutically active substance, comprising administering to this patient an effective amount of a tissue adhesive based on fibrinogen and a conjugate according to the present invention.

Thereby a depot of the pharmaceutically active substance with suitable releasing properties is provided which allows a suitable treatment of the patient with the pharmaceutical substance without the need of continuously and separately providing this substance.

The invention will now be explained in more detail by way of the examples and drawing figures to which, however, it shall not be restricted.

EXAMPLES

Within the present examples tumor necrosis factor (TNF) as an example for any pharmaceutically active substance is coupled via a commercially available TNF antibody to a fibrin binding substance. Thrombin and fibronectin have been selected as examples for substances having a fibrin/fibrinogen-binding moiety. Coupling of the antibody to thrombin and fibronectin has been achieved with 1-ethyl-3-(3-dimethyl-aminopropyl)carbodiimid (EDC). With this type of reaction the carboxy groups of a coupling component have been activated with EDC; these activated carboxy groups react with amino groups of the other component. Since the properties of the moieties may be different depending on which component is activated first, always both possibilities or variations have been investigated. In the following examples conjugate A-B means that component A is the component which is activated at the carboxy groups and component B is bound via its amino group. The proof of a successful coupling and the detection of the individual binding affinities (TNF-antibody, thrombin/fibronectin-fibrin) was analyzed via sandwich-ELISA.

Example 1

Coupling of TNF Antibody to Thrombin

Figure 2:
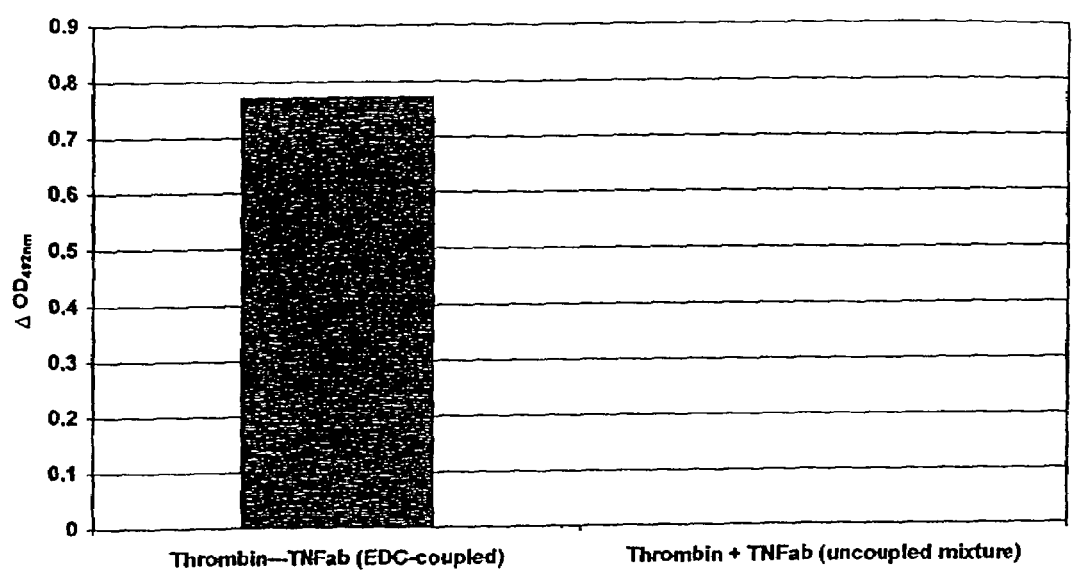
FIG. 2 shows the binding of TNF to a fibrinogen matrix via a TNF antibody coupled to thrombin.

A commercially available TNF antibody was coupled to thrombin via EDC. The proof for coupling and the individual binding affinities in the conjugates was detected via sandwich-ELISA (FIG. 1). Briefly, a microtiter plate was coated with fibrinogen and subsequently incubated with a complex (thrombin-TNF antibody or TNF antibody-thrombin), with TNF, with a secondary TNF antibody and with an enzyme conjugate recognizing the secondary antibody. This enzyme transforms a colorless substrate to a colored compound which is subsequently detectable. The turnover of the substrate is only possible if both components (TNF antibody and thrombin) have been covalently coupled by the EDC reaction and both binding affinities have been preserved. Thrombin-TNF antibody as well as TNF antibody-thrombin give positive reaction in this system (FIG. 2). Unmodified TNF antibody used as a control could not bind TNF to the fibrinogen matrix.

Example 2

Coupling of TNF Antibody to Fibronectin

Figure 3:
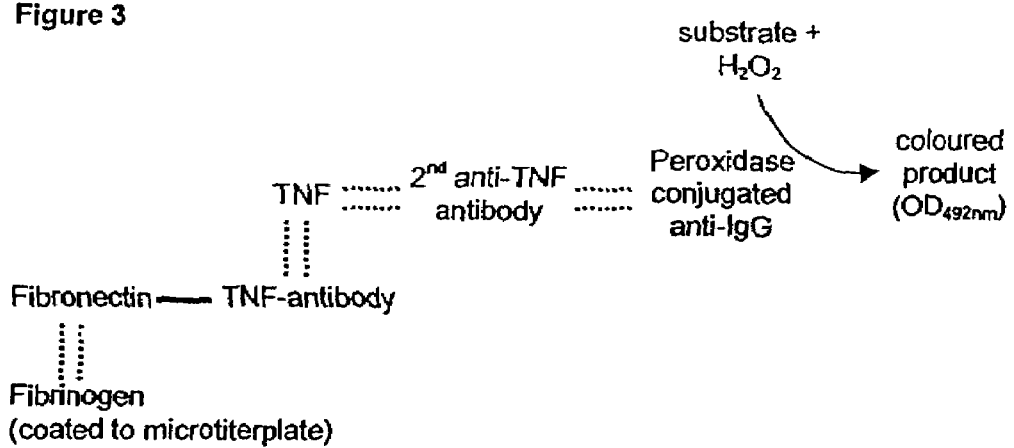
FIG. 3 shows the ELISA-sandwich system for the detection of covalent binding (–) of a TNF antibody and fibronectin and their binding affinities (:::) to fibrin/fibrinogen and TNF, respectively.
Figure 4:
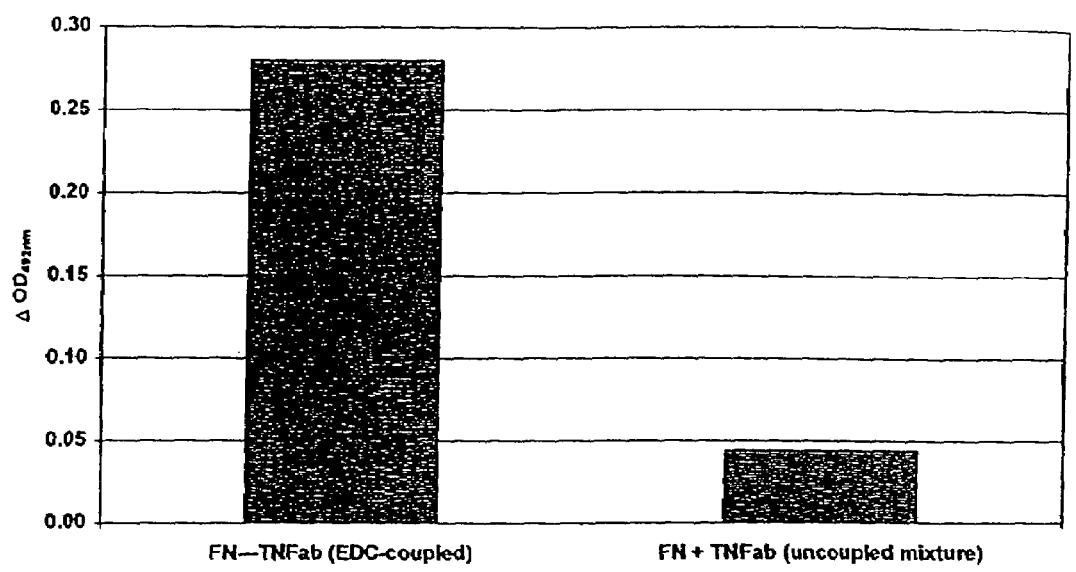
FIG. 4 shows the binding of TNF to a fibrinogen matrix via a TNF-antibody coupled to fibronectin.

A commercially available TNF antibody was coupled to fibronectin using EDC. The proof for coupling and the detection of the individual binding affinities in the conjugates was performed via sandwich-ELISA (FIG. 3), as in example 1. Fibronectin-TNF antibody as well as TNF antibody-fibronectin showed positive reaction in the present system (FIG. 4). A mixture of TNF antibody and fibronectin as control showed only a low binding of TNF to the fibrinogen matrix.

Example 3

Retarded Liberation of TNF from a Tissue Adhesive Clot

Figure 5:
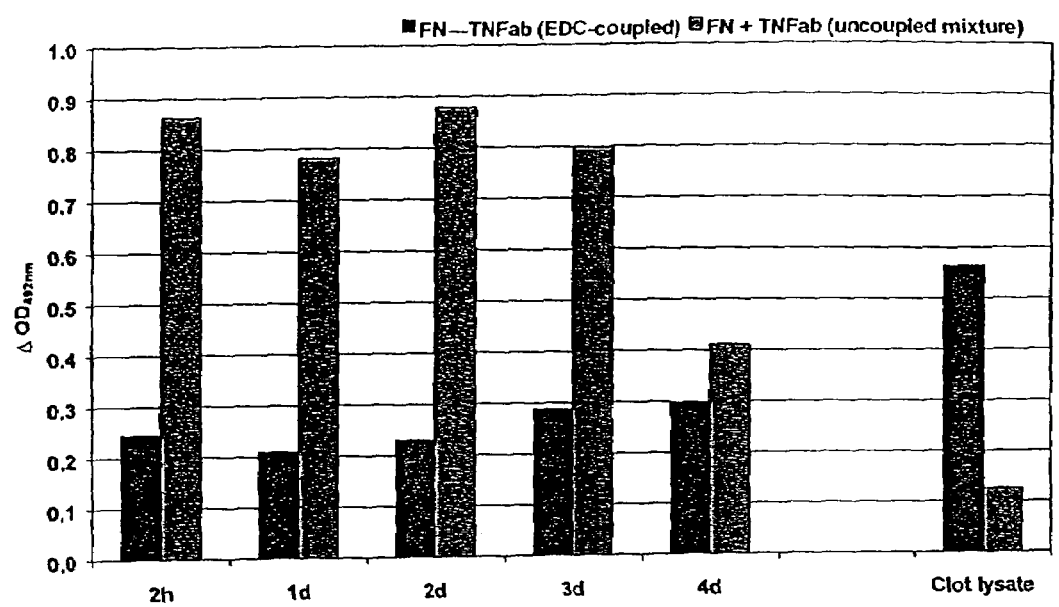
FIG. 5 shows the retention of TNF using the conjugate according to the present invention compared to the retention of TNF in the presence of uncoupled fibronectin and TNF antibody.

The proof for efficient retardation of TNF in a tissue adhesive clot based on fibrinogen was performed by adding TNF and fibronectin-TNF antibody complex as described in example 2 to the fibrinogen component of a fibrin sealant. In control experiments TNF and a mixture of fibronectin and TNF antibody have been added to this fibrinogen component. The fibrin clots were produced with such modified fibrinogen components and transferred to PBS 60 min after clotting. The clots then were incubated at 37° C. and PBS supernatants were substituted with fresh PBS at defined time periods. TNF content in these supernatants were detected (FIG. 5). After 12 days the clots were lysed with urokinase and the TNF content in the lysate was detected.

Addition of the fibronectin-TNF antibody complex to the fibrinogen component of the tissue adhesive resulted in a significant retardation of the liberation of TNF compared to the addition of a fibronectin-TNF antibody mixture. This was shown by reduced initial liberation of TNF in the PBS supernatants (days 1–3) as well as by a higher TNF content in the clot lysate after 12 days incubation in PBS (FIG. 5). Since fibrin dots have only been incubated in PBS and not been exposed to proteolytic digestion, the liberation of the TNF detected was mainly due to diffusion from the fibrin clot. Incubation with addition of proteases (e.g. urokinase) results in a continuous liberation of TNF over a longer period of time.

Example 4

Binding of Aprotinin Via Fibronectin

Based on the covalent binding of an active substance, in this case a fibrinolysis inhibitor, to a fibrin-binding anchor, in this case fibronectin, the delayed release of the fibrinolysis inhibitor from a fibrin clot into the surrounding medium can be shown.

A fibronectin-aprotinin conjugate was formed as described earlier. This conjugate was dissolved in the fibrinogen component before mixing with thrombin to ensure a homogeneous distribution of the conjugate in the fibrin clot. The clots were incubated in phosphate buffered saline (PBS) at 37° C. The PBS-supernatants were changed several times and clot persistence was either checked visually or determined by measuring the protein concentration in the PBS-supernatants.

Figure 6:
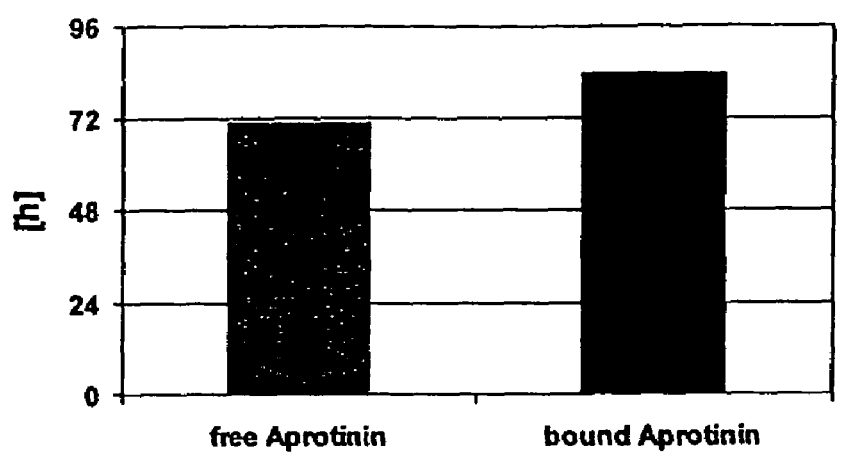
FIG. 6 shows the stability of fibrin-clots in hours with 3000 KIU/ml of free aprotinin or with 3000 KIU/ml bound aprotinin.

The aprotinin-fibronectin conjugate increased clot persistence compared to fibrin-clots supplemented with the same activity of non-conjugated aprotinin. This increase in clot persistence may be caused by a reduced release of the conjugate from the clot into the PBS compared to non-conjugated aprotinin (FIG. 6).

Example 5

Binding of Bacterial Fibrin Binding Protein fbe

Figure 7:
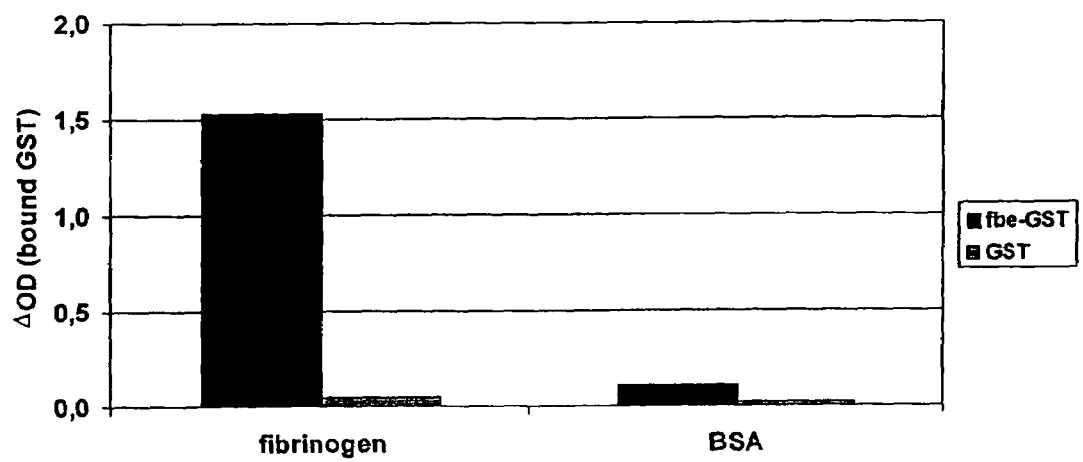
FIG. 7 shows the specific binding of fbe-GST but not GST alone to fibrinogen.

Another example for a fibrin-binding anchor is the bacterial protein fbe of *streptococcus epidermidis*. This protein was expressed as a fusion-protein with glutathione-S-transferase (GST) as the active part. Lysates from bacteria expressing either the fusion-protein fbe-GST or GST alone were adjusted to contain the same activity of GST and applied to fibrinogen- or BSA-coated ELISA-plates. Bound GST was detected by an anti-GST antibody. The fusion-protein fbe-GST binds specifically to fibrinogen via its fbe-domain. The fusion-protein does not bind to bovine serum albumin (BSA) which served as a control for unspecific protein-protein interaction. GST alone lacking the fbe-domain does not bind to fibrinogen (FIG. 7).

Example 6

DNA as a Fibrin/Fibrinogen Anchor

DNA binds very strong to fibrin/fibrinogen. Therefore a piece of DNA was embedded in a fibrin sealant matrix and its affinity for fibrin/fibrinogen lead to a slow but sustained release of DNA over a long period of time. For the purposes of the present invention DNA is preferably used in either form, which means single- or double stranded DNA, linear or circular DNA, as a fibrin/fibrinogen-binding moiety.

Figure 8A:
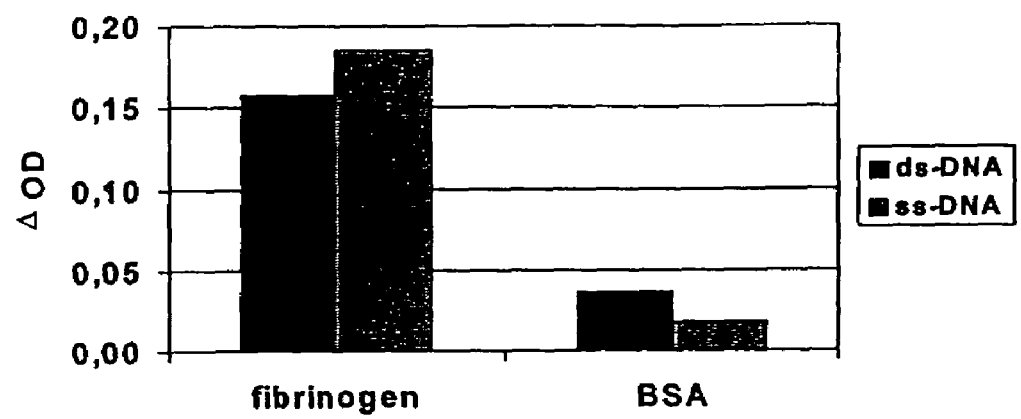
FIG. 8a shows the specific binding of biotinylated double stranded (ds) and single stranded (ss) DNA to fibrinogen but not to BSA.
Figure 8B:
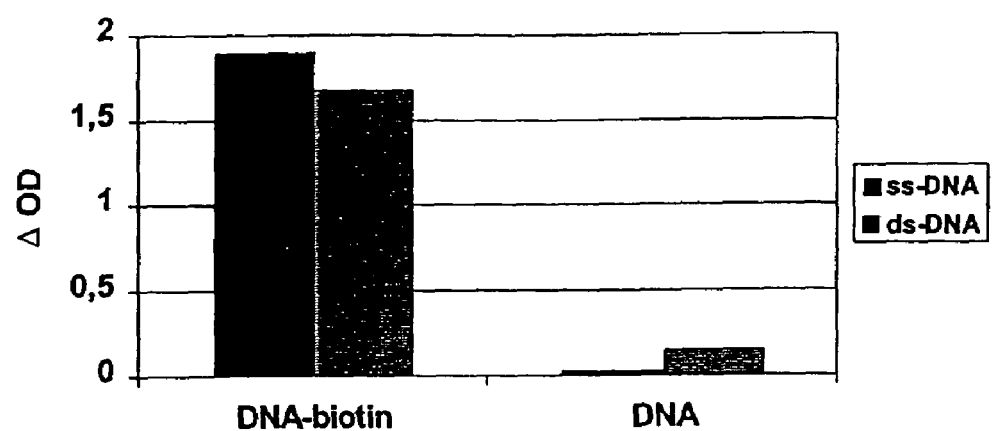
FIG. 8b shows the binding of Streptavidin-Peroxidase (SV-POX) preincubated with biotinylated DNA to a fibrinogen matrix via the DNA as fibrin sealant-binding moiety.

For the present experiment a biotinylated single-stranded oligodeoxynucleotide (20 b) and a biotinylated double-stranded DNA (700 b) were synthesized. The biotinylated DNA molecules were mixed with a streptavidin-peroxidase conjugate to form an affinity based complex. The complexes were applied to fibrinogen or BSA-coated ELISA-plates and the bound peroxidase-activity was measured. Peroxidase was specifically bound to fibrinogen coated wells via the DNA as a fibrin/fibrinogen-binding moiety. No binding to BSA was observed and to avoid false positive results due to unspecific binding of streptavidin-peroxidase to DNA a control experiment was carried out with unbiotinylated DNA showing no signal (FIGS. 8a and 8b).

Example 7

Thrombin as a Fibrin/Fibrinogen Anchor

Thrombin has a fibrinogen cleaving activity and a fibrin/fibrinogen-binding activity. The two activities are located at distinct sites in the molecule. For the present experiment biotinylated albumin was mixed to a fibrin clot either as such (=free form) or bound via a thrombin-PPACK (=D-Phe-Pro-Arg-Chlormethylketon) anchor (=covalently bound form). Biotin was used as marker to measure the release of both forms of albumin.

Figure 9:
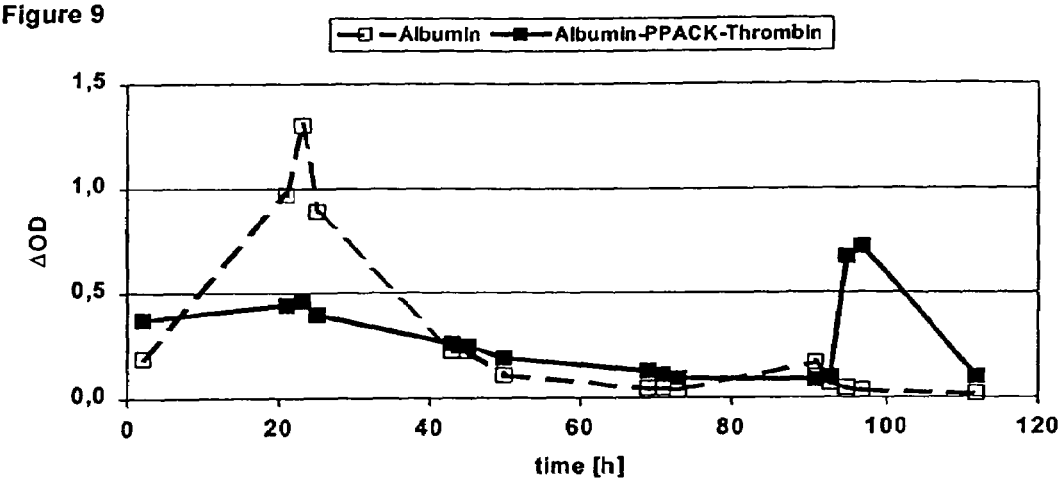
FIG. 9 shows the release rate of a biotinylated albumin that is covalently bound to thrombin compared to the release of free biotinylated albumin from a fibrin clot.

As shown in FIG. 9, the covalently bound albumin is retarded in the fibrin sealant clots for 4 days, whereas the free albumin is released within 1 day.

Example 8

Fibrin-Binding Recombinant Fusion Protein

FIG. 11 shows the recombinant fusion protein produced for this example [SEQ ID NO:1]. The C-terminal portion of $VEGF_{165}$ which is the fibrin-binding portion of this fusion protein, is fused to leptin, which is one example of a pharmaceutically active substance. The fusion protein contains a natural plasmin cleavage site derived from $VEGF_{165}$. At C146, the final residue in full-length leptin overlaps with the first Cys in the $VEGF_{165}$ C-terminal domain.

Figure 12:
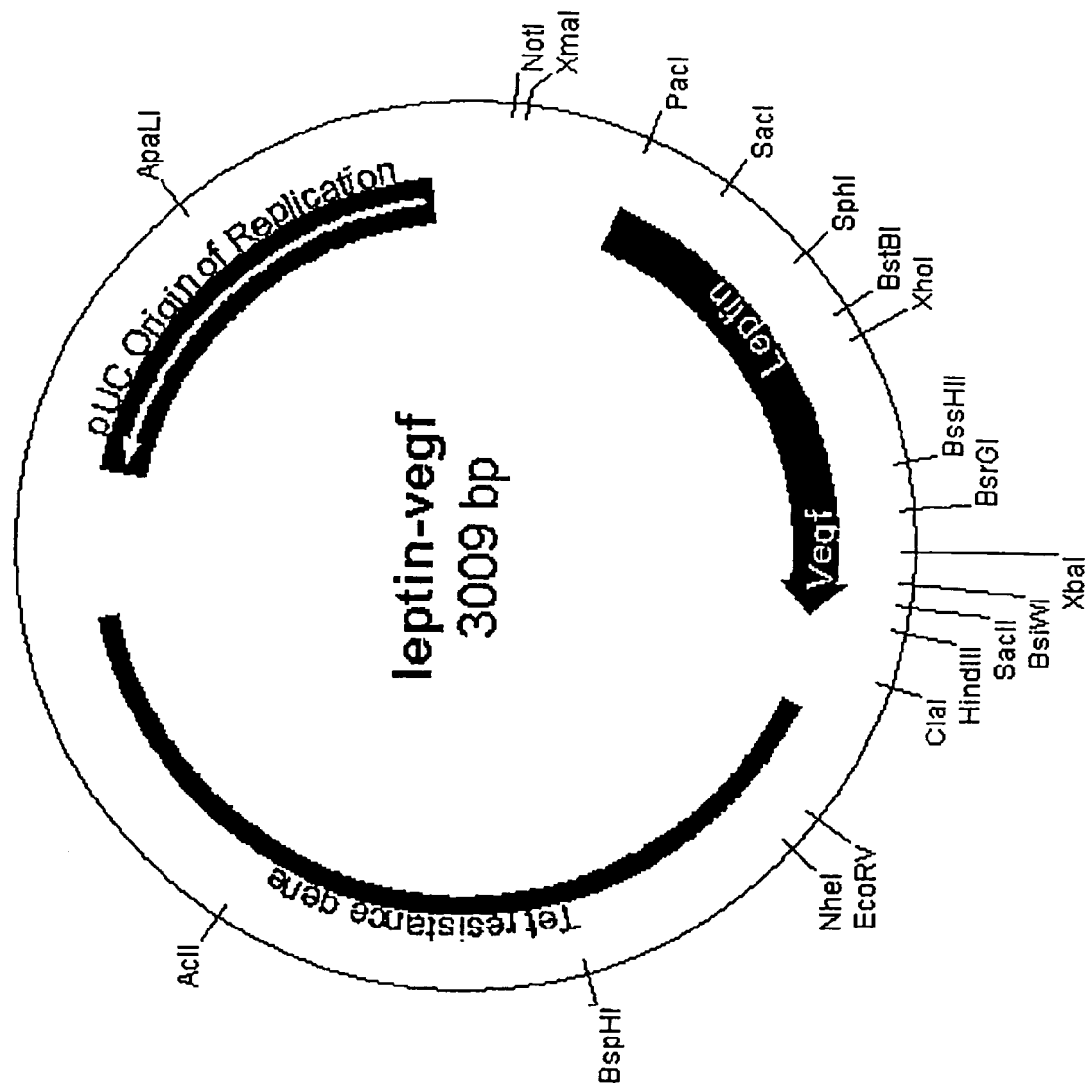
FIG. 12 depicts the expression plasmid containing the cassette encoding the leptin- VEGF$_{165}$ C-terminal-His tag fusion protein.

The DNA construct encoding the leptin-$VEGF_{165}$ fusion protein was inserted into the plasmid shown in FIG. 12 using the HindIII and PacI restriction sites. The plasmid was then transfected into *E. coli*, and the fusion protein was expressed by the bacteria.

The fusion protein is purified from the bacteria using techniques well known in the art of genetic engineering. The fusion protein is then incorporated into a fibrin clot, wherein the $VEGF_{165}$ C-terminal moiety binds to the fibrin in the clot. The resulting clot forms a depot for the sustained release of leptin, which is known to be a promoter of wound healing. When the clot is placed in a wound site, the natural plasminogen in the patient's plasma entering the wound is converted to plasmin, which in turn cleaves the fusion protein, thereby releasing the leptin moiety to diffuse from the clot to act in healing. Another mechanism for release is based on the dissociation rate of the $VEGF_{165}$ C-terminal domain from fibrin; according to this mechanism, the entire conjugate is released and diffuses from the clot, allowing the leptin moiety to act at the wound site, outside the clot.

What is claimed is:

1. Fibrin/fibrinogen-binding conjugate comprising
   a fibrin/fibrinogen-binding moiety that is a nucleic acid,
   a substance capturing moiety capable of reversibly binding to a pharmaceutically active substance,
   wherein said fibrin/fibrinogen-binding moiety is bound to said substance capturing moiety.

2. The conjugate of claim 1, wherein said substance capturing moiety is an antibody, a receptor or a part thereof which specifically recognizes said pharmaceutically active substance.

3. The conjugate of claim 1, further comprising a pharmaceutically active substance.

4. The conjugate of claim 3, wherein said pharmaceutically active substance is selected from the group consisting of antibiotics, growth factors, receptors for tissue components, tissue adhesive substances, nucleic acids, plasma proteins, hormones, heparinoids, wound-healing substances, and imaging agents.

5. The conjugate of claim 1, wherein said fibrin/fibrinogen-binding moiety and said substance capturing moiety are covalently bound.

6. Fibrin/fibrinogen-binding conjugate comprising
   a fibrin/fibrinogen-binding moiety selected from the group consisting of fibronectin, bacterial fibrinogen binding proteins, integrins, and moieties derived from any member of this group,
   a substance capturing moiety that is an antibody or a part thereof which specifically recognizes a pharmaceutically active substance, and
   the pharmaceutically active substance,
   wherein said fibrin/fibrinogen-binding moiety is bound to said substance capturing moiety.

7. Fibrin/fibrinogen-binding conjugate comprising
   a fibrin/fibrinogen-binding moiety selected from the group consisting of fibronectin, bacterial fibrinogen binding proteins, integrins, and moieties derived from any member of this group,
   a substance capturing moiety that is an antibody or a part thereof which specifically recognizes a pharmaceutically active substance,
   wherein said fibrin/fibrinogen-binding moiety is bound to said substance capturing moiety.

8. The conjugate of claim 6, wherein said pharmaceutically active substance is selected from the group consisting of antibiotics, growth factors, receptors for tissue components, tissue adhesive substances, nucleic acids, plasma proteins, hormones, heparinoids, and imaging agents.

9. The conjugate of claim 6, wherein said fibrin/fibrinogen-binding moiety and said substance capturing moiety are covalently bound.

10. The conjugate of claim 6, wherein said pharmaceutically active substance is a wound healing substance.

11. The conjugate of claim 7, wherein said fibrin/fibrinogen-binding moiety and said substance capturing moiety are covalently bound.

12. The conjugate of claim 7 wherein said pharmaceutically active substance is selected from the group consisting of antibiotics, growth factors, receptors for tissue components, tissue adhesive substances, nucleic acids, plasma proteins, hormones, heparinoids, and imaging agents.

13. The conjugate of claim 7, wherein said pharmaceutically active substance is a wound healing substance.

* * * * *

UNITED STATES PATENT AND TRADEMARK OFFICE
CERTIFICATE OF CORRECTION

PATENT NO. : 7,091,325 B2
APPLICATION NO. : 10/749832
DATED : August 15, 2006
INVENTOR(S) : H. Redl et al.

It is certified that error appears in the above-identified patent and that said Letters Patent is hereby corrected as shown below:

On the front page of the letters patent:

"Inventors:     Heinz Redl, Vienna (AT); Walter Fuerst, Vienna (AT): Rudolf Kneidinger, Vienna (AT): Sam L. Helgerson, Altadena, CA (US); Douglas, Looker, Ft. Lupton, CO (US); Elisabeth M. Inman, Pasadena, CA (US); Jane P. Richards, Longmont, CO (US); Catalina Wong, Los Angeles, CA (US)"

should read     Item [76]

--Inventors:    Heinz Redl, Vienna (AT); Walter Fuerst, Vienna (AT); Rudolf Kneidinger, Vienna (AT)--

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,091,325 B2  Page 1 of 1
APPLICATION NO. : 10/749832
DATED : August 15, 2006
INVENTOR(S) : Redl H. et al.

It is certified that error appears in the above-identified patent and that said Letters Patent is hereby corrected as shown below:

On the Title page of the letters patent:

Item [75]
"Inventors: Heinz Redl, Vienna (AT); Walter Fuerst, Vienna (AT); Rudolf Kneidinger, Vienna (AT); Sam L. Helgerson, Altadena, CA (US); Douglas, Looker, Ft. Lupton, CO (US); Elisabeth M. Inman, Pasadena, CA (US); Jane P. Richards, Longmont, CO (US); Catalina Wong, Los Angeles, CA (US):

Title page should read
Item [75]

--Inventors: Heinz Redl, Vienna (AT); Walter Fuerst, Vienna (AT); Rudolf Kneidinger, Vienna (AT)--

Signed and Sealed this

Ninth Day of January, 2007

JON W. DUDAS
*Director of the United States Patent and Trademark Office*